United States Patent
Jeon et al.

(10) Patent No.: US 8,380,834 B2
(45) Date of Patent: Feb. 19, 2013

(54) SYSTEM AND METHOD FOR SUPPORTING INFORMATION INTEROPERABILITY BETWEEN MEDICAL INSTRUMENTS

(75) Inventors: Jin-Ok Jeon, Seoul (KR); Jae-Young Soh, Seoul (KR); Si-Hoon Ahn, Seongnam-si (KR); Hyung-Jong Jang, Seoul (KR); Eung-Hwan Kim, Seoul (KR); Dong-Uk Kim, Chuncheon-si (KR)

(73) Assignee: Bit Computer Co., Ltd., Seoul (KR)

( * ) Notice: Subject to any disclaimer, the term of this patent is extended or adjusted under 35 U.S.C. 154(b) by 421 days.

(21) Appl. No.: 12/672,864

(22) PCT Filed: Dec. 3, 2009

(86) PCT No.: PCT/KR2009/007180
§ 371 (c)(1),
(2), (4) Date: Feb. 9, 2010

(87) PCT Pub. No.: WO2010/067981
PCT Pub. Date: Jun. 17, 2010

(65) Prior Publication Data
US 2011/0035627 A1    Feb. 10, 2011

(30) Foreign Application Priority Data

Dec. 12, 2008  (KR) .................. 10-2008-0126329

(51) Int. Cl.
*G06F 15/173* (2006.01)
(52) U.S. Cl. ......... 709/223; 709/203; 709/224; 709/231
(58) Field of Classification Search .................. 709/201, 709/203, 223, 224, 231; 705/2, 3; 707/10
See application file for complete search history.

(56) References Cited

U.S. PATENT DOCUMENTS

| | | | |
|---|---|---|---|
| 2002/0059257 A1* | 5/2002 | Matsumura et al. | 707/10 |
| 2006/0173713 A1* | 8/2006 | Petro et al. | 705/2 |
| 2007/0233035 A1* | 10/2007 | Wehba et al. | 709/238 |
| 2007/0250130 A1* | 10/2007 | Ball et al. | 607/32 |
| 2008/0097795 A1* | 4/2008 | Sasai et al. | 705/3 |

* cited by examiner

Primary Examiner — Ramy M Osman
(74) Attorney, Agent, or Firm — IPLA P.A.; James E. Bame

(57) ABSTRACT

The present invention relates, in general, to Electronic Medical Record (EMR) systems, and, more particularly, to a system and method for supporting information interoperability between medical instruments which is capable of automatically combining medical test information measured by a plurality of medical instruments for performing data communication in compliance with various data interface protocols with the medical information of an EMR system.

10 Claims, 11 Drawing Sheets

SYSTEM AND METHOD FOR SUPPORTING INFORMATION INTEROPERABILITY BETWEEN MEDICAL INSTRUMENTS

CROSS REFERENCE

This application claims priority of International Application No. PCT/KR2009/007180 filed 3 Dec. 2009, which claims priority under the Paris Convention to Korean Patent Application No. 10-2008-0126329, filed 12 Dec. 2008 with the Korean Intellectual Property Office.

BACKGROUND OF THE INVENTION

1. Technical Field

The present invention relates, in general, to Electronic Medical Record (EMR) systems, and, more particularly, to a system and method for supporting information interoperability between medical instruments which is capable of automatically combining medical test information measured by a plurality of medical instruments for performing data communication in compliance with various data interface protocols with the medical information of an EMR system.

2. Description of the Related Art

Due to the development of information and communication technology, computer-based patient recording has become popularized in the medical field. Medical information includes not only personal text information, such as family clinical history records, past clinical history records and metal disease records, but also image information, such as X-rays. This type of medical information is being freely moved between internal and external computers and between medical institutions over communication networks.

Representative systems for processing and managing such medical information include EMR systems and Picture Archiving and Communication Systems (PACSs). An EMR system is a system which is capable of putting medical examination and treatment records such as hospital admission records, first ambulatory examination records, second ambulatory examination records, problem lists, development records, surgery/anesthesia records, hospital discharge summaries, consultative medical examination and treatment records and special treatment records, nursing records such as prescription and performance records, nursing histories, clinical observation records, special measurement records, nursing procedures, discharge nursing records, surgery nursing records and recovery nursing records, patients' affairs department records such as patient basic information and patient reception information, medical examination and treatment support records such as patient test results, and prescription records such as medicine/injection prescription, test prescription and treatment/surgery prescription records, into an integrated database and then managing all information of patients without requiring charts in an integrated manner. Accordingly, the EMR system provides advantages in that the chart management cost, the manpower cost and various types of costs for printing can be reduced because medical, nursing, patients' affairs department, prescription and patient test result data, etc. which were manually recorded in charts in relevant periods are computerized and managed without using charts, and in that medical accidents can be prevented, the efficiency of medical examination and treatment can be improved and redundant work can be reduced, and business and management based on various types of statistics can be efficiently performed because interoperability is automatically applied to various types of information about patients.

A PACS is an image storage and transmission system, and is a system which stores and manages captured medical images in the form of digital data without requiring films required by conventional analog medical imaging instruments such as X-ray machines and Computed Tomography (CT) machines. A PACS provides the advantage of avoiding expenses required for the management and purchase of films because films are not required, and the advantage of improving the efficiency of medical examination and treatment because captured medical images can be viewed and diagnoses can be made from anywhere.

However, a conventional EMR system computerizes only text-based information manually recorded by doctors, nurses, patients' affairs department staffs, etc., but has the problem of not supporting interoperability between the pieces of test information measured by a plurality of medical instruments having various data interface standards. That is, since a plurality of medical instruments have different data interface standards, they cannot operate in conjunction with an EMR system.

Furthermore, in order to manage test information measured by medical instruments using the EMR system, a problem arises in that the test information manually measured must be digitized, so that time and man power are required, and this required man power results in high expenses.

In order to solve the problem, respective medical instruments require gateway devices for digitizing measured test information, as shown in FIG. 1.

FIG. 1 is a drawing showing the configuration of a medical measurement data interoperability EMR system equipped with gateway devices connected to medical instruments in a one-to-one correspondence.

Referring to FIG. 1, the typical medical measurement data interoperability EMR system includes gateway devices 40 connected to a plurality of medical instruments 10 having various data interface standards via data interface units 21 corresponding to the medical instruments 10, and configured to convert a received measured signal into the data format required by an EMR system 40 and send it over a local network 45, a database 35 configured to store EMR information, and a hospital server 30 configured to record the resulting measured information, from the medical instruments 10, in the database 35 in association with the EMR information. The measured signal may be an analog image signal or text-based serial or parallel data according to each type of medical instrument 10.

As described above, the typical medical measurement data interoperability EMR system has the problem that, in order to support interoperability with the information of a typical EMR system 40, the respective medical instruments 10 are provided with interface units 21 based on corresponding data interface standards and furthermore gateway devices 20 are required for realizing conformity to the data format required by the EMR system 40, so that the setup cost of the system is high.

Furthermore, the conventional medical measurement data interoperability EMR system has the problem of PC-based manual work being required when providing measured information interoperability between the medical instruments and the EMR system 40 and when performing maintenance.

Furthermore, the conventional medical measurement data interoperability EMR system has the problem of lacking scalability because each of the gateway devices thereof can be used only for a medical instrument having the same data interface standard.

SUMMARY OF THE INVENTION

Accordingly, the present invention has been made keeping in mind the above problems occurring in the prior art, and an object of the present invention is to provide a system and method for providing interoperability of the information of medical instruments which is capable of collecting and combining medical test information measured by a plurality of medical instruments which perform data communication in compliance with various data interface protocols and which is capable of automatically combining the medical test information with the medical information of an EMR system.

Another object of the present invention is to provide a system and method for providing interoperability of the information of medical instruments which has medical instrument management functionality capable of medical instrument monitoring, error reporting and asset management.

In order to accomplish the above objects, the present invention provides a system for supporting information interoperability between medical instruments, including a plurality of medical instruments configured to have data interface units for sending and receiving data in compliance with preset interface protocols, and configured to, when receiving medical measurement commands via the data interface unit, perform medical measurement and then send medical measurement result information; an integrated gateway device configured to have a multiple interface unit comprising data interface units corresponding to the data interface units of the medical instruments, respectively, and configured to, when patient test information requesting medical measurement has been received, create and send waiting lists for respective medical instruments, send the medical measurement commands to relevant medical instruments in conformity with the received medical test command, and send medical test completion information, including the medical measurement result information received in response to the medical measurement commands, via a wired/wireless communication network; one or more user terminals configured to, when the waiting lists for respective medical instruments have been received, send medical test commands based on the waiting lists for respective medical instruments to the integrated gateway device; and a hospital server configured to have a database for storing Electronic Medical Record (EMR) information including medical measurement information, and configured to, when a test event has occurred, send the patient test information to the integrated gateway device, receive medical test completion information in response to the patient test information, and store the medical test completion information in association with relevant patient information of the EMR information.

The integrated gateway device includes a multiple interface unit comprising data interface units which correspond to the data interface units of the medical instruments, respectively; a first storage unit storing middleware capable of performing communication with the medical instruments which may be connected to the multiple interface unit and processing data for the communication; a wired/wireless communication unit for, when the medical test command is received, sending the medical test completion information to a wired/wireless communication network; and a control unit for, when the medical test command is received via the wired/wireless communication unit, sending a medical measurement command via the multiple interface unit, collecting pieces of medical measurement result information received in response to the medical test command and creating the medical test completion information, and sending the medical test completion information via the wired/wireless communication unit.

The multiple interface unit includes at least one parallel interface unit, at least one serial interface unit, at least one asynchronous serial bus interface unit, and at least one DICOM interface unit.

The multiple interface unit further includes an analog video interface unit, and the integrated gateway device further includes a digital conversion unit for converting an analog video signal, received through the analog video interface unit, into digital image data and outputting the digital image data.

The multiple interface unit further includes an external memory interface unit which has a plurality of external memory slots and which reads data from external memory inserted into the slots and outputs the data to the control unit or stores data, input from the control unit, in the external memory; and the control unit directs the external memory interface unit to read medical measurement result information from the external memory when a read command is input from one of the user terminals, and directs the external memory interface unit to store medical test completion information in the external memory when a write command is input from the user terminal.

It is preferable that the patient test information include information about a patient and a doctor in charge.

It is preferable that the medical test command include information about a patient, a doctor in charge, a medical instrument user and one or more medical instruments.

It is preferable that the medical measurement command include medical instrument information and an operation command.

It is preferable that the medical measurement result information include medical instrument information and medical measurement result data.

It is preferable that the medical test completion information include information about one or more medical instruments, a doctor in charge, a medical instrument user, a patient, and medical measurement result data.

It is preferable that the integrated gateway device perform a failure diagnosis by checking reception results of medical measurement result information based on the medical measurement command for the failure diagnosis and send the medical test completion information with failure diagnosis information based on the performance of the failure diagnosis included therein.

In order to accomplish the above objects, the present invention provides a method of supporting information interoperability between medical instruments, including a first step of a hospital server sending patient test information to a user terminal when a test event has occurred; a second step of, when the patient test information has been received from the hospital server, the user terminal sending a medical test command based on the patient test information and diagnosis information to an integrated gateway device; a third step of the integrated gateway device sending a medical measurement command to one or more relevant medical instruments included in the requested medical test command; a fourth step of, when receiving the medical measurement command, the medical instruments performing medical measurement and then sending medical measurement result information; a fifth step of the integrated gateway device receiving the medical measurement result information and sending medical test completion information including measurement result information over a wired/wireless communication network; and a sixth step of the hospital server receiving the medical test completion information and storing the medical test completion information in association with relevant patient information of the electronic medical record information.

The sixth step further includes the integrated gateway device, when receiving the medical measurement result information, performing a failure diagnosis by analyzing whether medical measurement result information in response to the medical measurement command has been received and the received medical measurement result information, creating failure diagnosis information, and sending the test completion information with the created failure diagnosis information included therein; the sixth step further includes the hospital server analyzing the failure diagnosis information included in the test completion information, and storing the measurement result information in association with relevant patient information of the EMR information depending on whether a failure has occurred or a type of failure.

The method further includes a seventh step of, when a failure has occurred at the sixth step, notifying a person in charge of the occurrence of the failure by sending failure information to a user terminal of the person in charge.

In order to accomplish the above objects, the present invention provides a system for supporting information interoperability between medical instruments, including a plurality of medical instruments configured to have data interface units for sending and receiving data in compliance with preset interface protocols, and configured to, when receiving medical measurement commands via the data interface units, perform medical measurement and then send medical measurement result information; an integrated gateway device configured to have a multiple interface unit comprising data interface units corresponding to the data interface units of the medical instruments, respectively, and configured to, when patient test information requesting medical measurement has been received, create, update and send waiting lists for respective medical instruments, send the medical measurement commands to relevant medical instruments in order of the waiting lists for respective medical instruments, and send medical test completion information, including the medical measurement result information received in response to the medical measurement commands, via a wired/wireless communication network; and a hospital server configured to have a database for storing EMR information including medical measurement information, and configured to, when a test event has occurred, send the patient test information to the integrated gateway device, receive medical test completion information in response to the patient test information, and store the medical test completion information in association with relevant patient information of the EMR information.

The system further includes one or more user terminals for receiving the created and updated waiting lists for respective medical instruments via the wired/wireless communication network and displaying them.

Accordingly, the system for supporting information interoperability between medical instruments according to the present invention has the advantage of automatically collecting a variety of types of heterogeneous output data and stably combining it with EMR information because the integrated gateway is employed.

Furthermore, the system for supporting information interoperability between medical instruments according to the present invention has the advantage of reducing the system setup cost because a plurality of pieces of heterogeneous data output from a plurality of medical instruments is collected using a single integrated gateway device.

Furthermore, the system for supporting information interoperability between medical instruments according to the present invention has the advantage of expanding ports by connecting genders, each having a plurality of ports, to each of the ports of the interface unit. That is, the present invention has the advantage of expanding add-on type medical instrument communication ports.

Furthermore, the system for supporting information interoperability between medical instruments according to the present invention has the advantage of enabling the failure of a medical instrument to be easily detected by performing error reporting based on medical instrument monitoring. Therefore, the present invention has the advantage of improving work efficiency by performing rapid troubleshooting.

Furthermore, the system for supporting information interoperability between medical instruments according to the present invention has the advantage of managing medical instrument assets because medical instrument management information, such as the registration, production/purchase date and number of tests of a newly purchased medical instrument, is held.

DESCRIPTION OF REFERENCE NUMERALS OF PRINCIPAL ELEMENTS IN THE DRAWINGS

| | |
|---|---|
| 110: medical instruments | 120: user terminal |
| 130: wired/wireless network | 140: hospital server |
| 150: database (DB) | 200: integrated gateway device |
| 210: control unit | 220: first storage unit |
| 230: second storage unit | 240: multiple interface unit |
| 250: digital conversion unit | 260: wireless communication unit |
| 270: wired communication unit | |

DETAILED DESCRIPTION OF THE INVENTION

The configuration and operation of a system for providing interoperability of the information of medical instruments according to the present invention will be described below with reference to the drawings.

Figure 1:
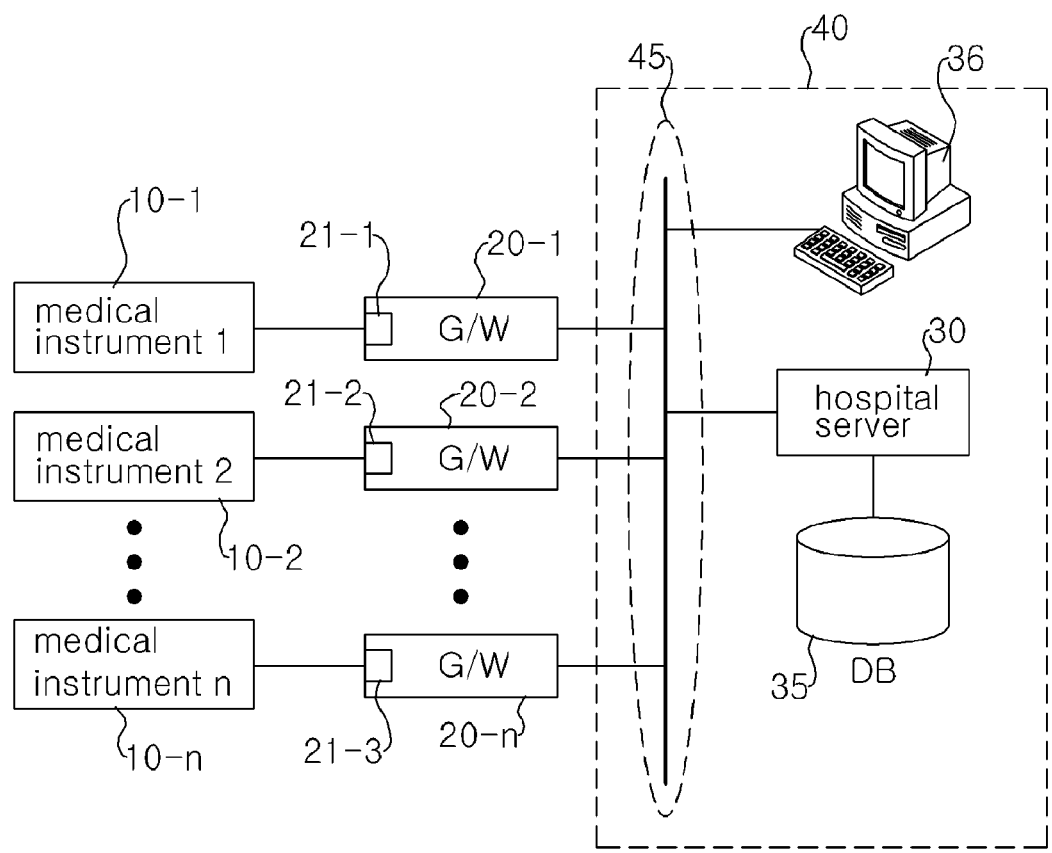
FIG. 1 is a drawing showing the configuration of an EMR system having a typical medical instrument interoperability function.
Figure 2:
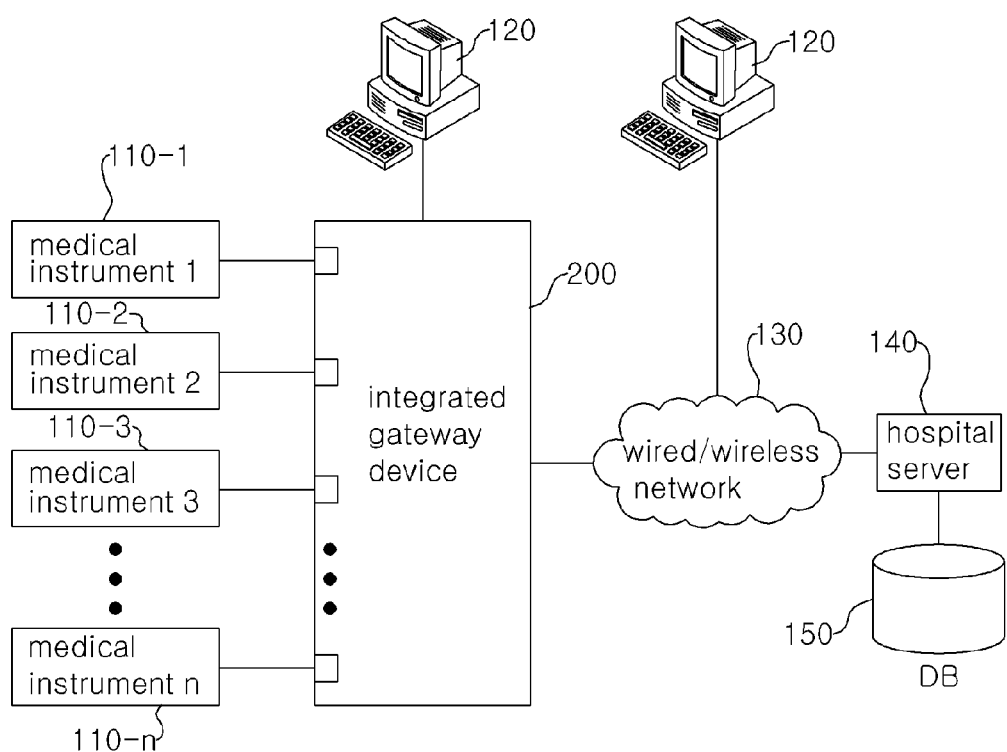
FIG. 2 is a diagram showing the configuration of a system for supporting information interoperability between medical instruments according to the present invention.

FIG. 2 is a diagram showing the configuration of the system for providing interoperability of the information of medical instruments according to the present invention.

The system for providing interoperability of the information of medical instruments according to the present invention includes a plurality of medical instruments 110, an integrated gateway device 200, user terminals 120, a wired/wireless network 130, a hospital server 140, and a database 150.

The medical instruments 110 include image medical instruments for capturing the organs of the bodies of patients, such as X-ray machines, Computed Tomography (CT) machines and Magnetic Resonance Imaging (MRI) machines, medical instruments for measuring the working status of various patient organs, such as electrocardiographs and sphygmomanometers, and clinical instruments for measuring and analyzing the numerical values of the various elements of specimens obtained from the bodies of patients or collected from nature. These medical instruments 110 perform corresponding measurements, and output measured data to external devices in compliance with preset data output interface protocols (standards). In general, in order to output measured data to the outside in compliance with the set data output interface protocols, the medical instruments 110 include data interface units which input and output data in compliance with the set data interface protocols. The data interface standards applied to the medical instruments 110 include a variety of standards such as a serial interface standard, a parallel interface standard, a Universal Serial Bus (USB) interface standard, a DICOM interface standard, an external memory interface standard, and an analog audio interface standard.

In order to receive and send signals from and to the medical instruments 110, the integrated gateway device 200 supports a multiple interface standard which supports data interface standards which may be required by the medical instruments 110. The integrated gateway device 200 supports wired/wireless data communication with the user terminal 120 and the hospital server 150 over the wired/wireless network 130. The wired and wireless data communication method may be Zigbee, or a TCP/IP protocol-based Wireless Local Area Network (LAN) or wired LAN method. Furthermore, the integrated gateway device 200 provides a web-based Graphic User Interface (GUI) to the accessing user terminal 120. The integrated gateway device 200 receives a medical test request from the user terminal 120 or hospital server 150, sets up a schedule, requests medical measurement according to the schedule based on the data interface standard of a corresponding medical instrument 110, and provides corresponding medical result information to the hospital server 150.

The wired/wireless network 130 may be a Zigbee-based PAN, LAN or Wireless LAN.

The user terminal 120 is connected to the integrated gateway device 200 by the wired/wireless network 130 or is connected directly to the integrated gateway device 200 and then performs data communication. Furthermore, the user terminals 120 perform data communication with the hospital server 140 over the wired/wireless communication network 130 or via the integrated gateway device 200 and the wired/wireless network 130. The user terminals 120 may be the computers or Personal Digital Assistants (PDAs) of persons or doctors in charge of the medical instruments who are directly using the medical instruments 110.

The hospital server 140 is provided with the database 150 for storing electronic medical record information including medical measurement information, and confirms the medical result information received from the integrated gateway devices 200 or user terminals 120 to EMR information and manages it in an integrated manner. Furthermore, the hospital server 140 further includes the unique number of each medical instrument, and a production or registration date and the number of tests for each unique number in the database 150 or a separate database (not shown), so that the hospital management can easily manage medical instrument assets and perform maintenance.

Figure 3:
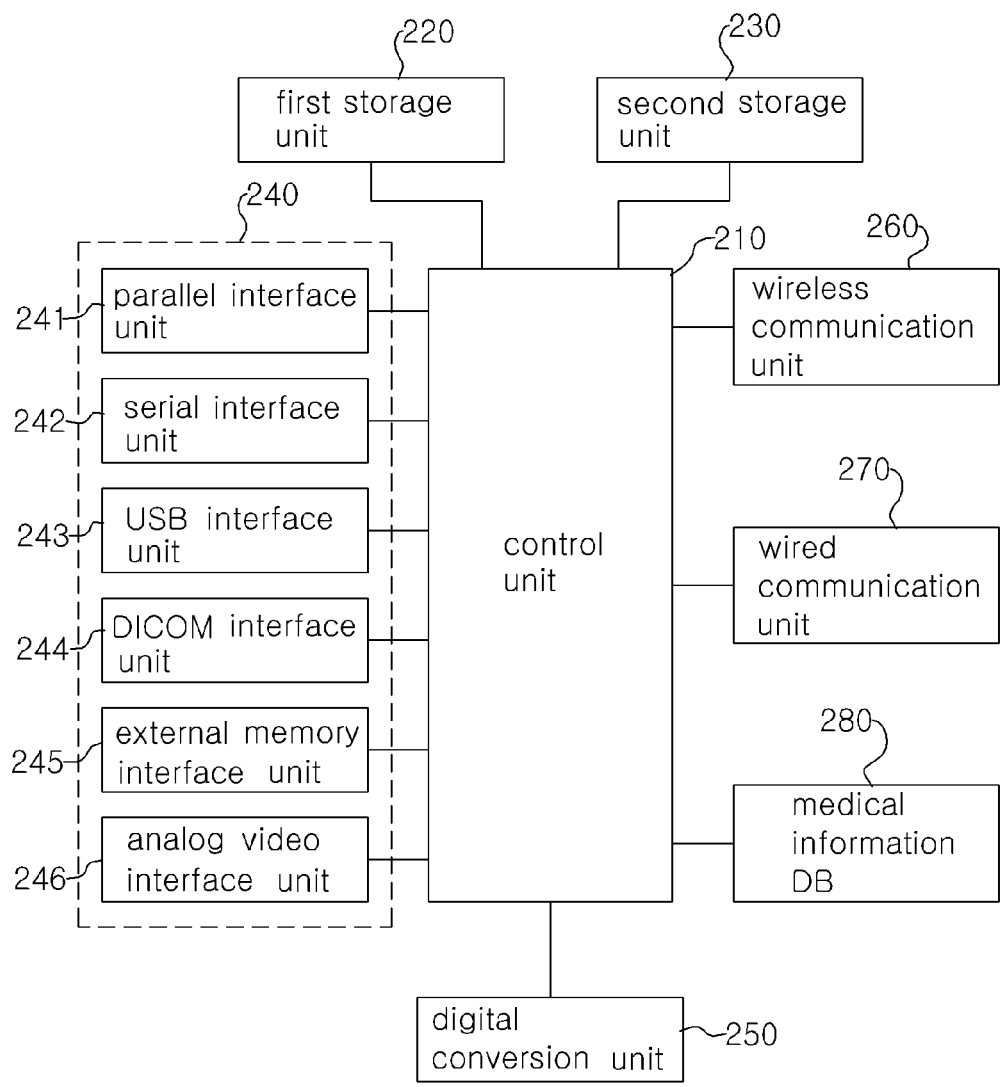
FIG. 3 is a diagram showing the configuration of the integrated gateway device of the system for supporting information interoperability between medical instruments according to the present invention.

FIG. 3 is a diagram showing the configuration of the integrated gateway device of the system for supporting information interoperability between medical instruments according to the present invention.

The configuration of the integrated gateway device 200 will be described in detail below with reference to FIG. 3.

The integrated gateway device 200 includes a control unit 210, a first storage unit 220, a second storage unit 230, a multiple interface unit 240, a digital conversion unit 250, a wireless communication unit 260, a wired communication unit 270, and a medical information DB 280.

The control unit 210 controls the overall operation of the integrated gateway device 200 according to the present invention.

Figure 5:
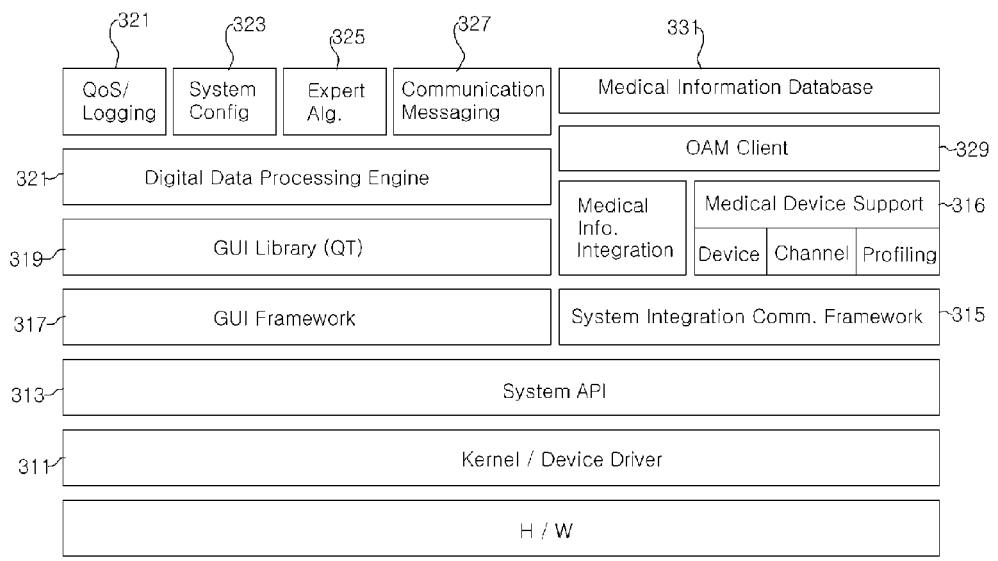
FIG. 5 is a diagram showing the middleware structure of the integrated gateway device according to the present invention.

The first storage unit 220 stores a control program having the structure of middleware M/W, such as that shown in FIG. 5, so as to control the operation of the integrated gateway device according to the present invention. The structure of the middleware will be illustrated in detail in FIG. 5.

The second storage unit 230 temporarily stores data generated by the operation of the control unit 210.

Figure 4:
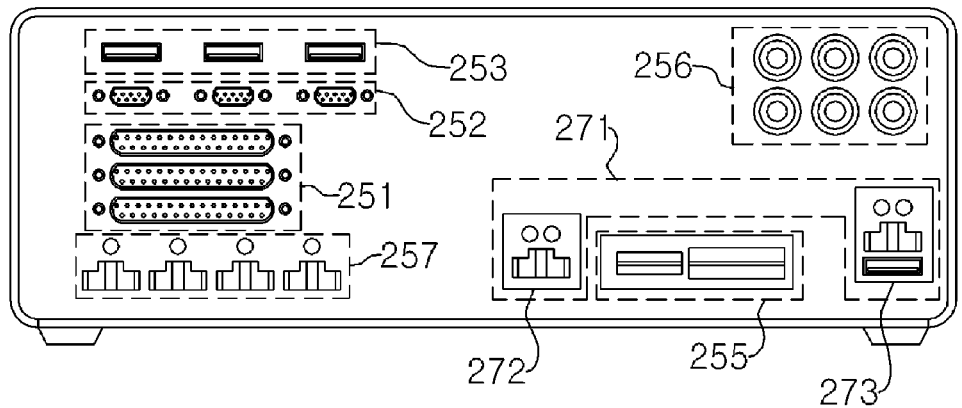
FIG. 4 is a diagram showing the port configuration of the multiple interface unit of the integrated gateway device shown in FIG. 3.

The multiple interface unit 240 sends and receives analog signals and digital data to and from medical instruments having various data interface standards. The multiple interface unit 240 may include a parallel interface unit 241, a serial interface unit 242, a USB interface unit 243, a DICOM interface unit 244, an external memory interface unit 245, and an analog video interface unit 246. Although the DICOM interface unit 244 is an interface unit for supporting Ethernet communication, it is included in the multiple interface unit 240 in the sense that it is connected to the medical instruments 110 for outputting DICOM data. Accordingly, the user terminal 120 may be connected to the DICOM interface unit 244. Each of the interface units may be configured such that each of the interface units 241, 242, 243, 244 and 246 includes one or more ports, as shown in FIG. 4. The ports for the same interface unit are distinguished from each other by the channel allocation of the control unit 210. Furthermore, each port can be expanded by connecting a gender having two or more ports to the port. For this purpose, a kernel/device driver layer 311 which will be described in conjunction with FIG. 5 below must support firmware for supporting port expansion.

The external memory interface unit 245 is configured to read measured medical data stored in external memory or write medical test completion information.

The digital conversion unit 250 converts an analog video signal input through the analog video interface unit 246 into a digital video signal, and outputs the digital video signal. The digital conversion unit 250 may be integrated with the analog video interface unit 246.

The wired communication unit 270 is connected to the wired network, LAN, WAN and/or PSTN of the wired/wireless communication network 130, and performs data communication with the user terminal 120 and the hospital server 140. Furthermore, a separate control port is provided as shown in FIG. 4, and direct connection to the user terminal 120', such as a console, and then data communication is performed.

The wireless communication unit 260 is connected to the wireless network of the wired/wireless communication network 130, and performs data communication with the user terminal 120 and the hospital server 140.

The medical information DB 280 stores a variety of types of medical information, such as personal information such as the name, age, height, weight and sex of each patient related to patients or specimens to be measured by the medical instruments 110 and medical data associated with test items, for example, a blood test and electrocardiography measured by the medical instruments 110, and also stores device management information, a supported medical instruments list and profile information, measurement log and log records regarding data exchange, and error occurrence information, etc. The medical information DB 280 supports the processing of general Structured Query Language (SQL) queries.

FIG. 4 is a diagram showing an example of the port arrangement of the multiple interface unit provided in the rear part of the integrated gateway device shown in FIG. 3. The multiple interface unit 240 includes three parallel ports 251, three serial ports 252, three USB ports 253, four DICOM ports 257 which are RJ45 ports, two RGB analog video ports 256, two control ports 271, and an external memory port 255 having external memory slots.

The control port 271 includes a server port 272 and a console port 273. The server port 272 is a WAN port, and is provided in the wired communication unit 270 shown in FIG. 3. The console port 273 is a port which is configured such that a console, such as the user terminal 110, can be directly connected thereto and perform data communication.

In addition to the ports and interface units, an RJ11 port and a telephone interface unit, that is, a telephone modem, is additionally provided, so that long distance data transmission and reception over a telephone line is enabled.

FIG. 5 is a drawing showing the middleware structure of the integrated gateway device according to the present invention.

Referring to FIG. 5, the first storage unit 220 is configured to have the structure of a memory stack, such as that shown in FIG. 4, so as to control the integrated gateway device 200. The memory stack according to the present invention includes a kernel/device driver layer 311, a system Application Programming Interface (API) layer 313, a System Integration Comm. Framework layer 315, a medical information layer 316, a GUI layer 317, a digital data processing layer 319, a QoS/logging layer 321, a system setting layer 325, an EXpert Alg layer 325, a communication messaging layer 327, an Operations, Administration and Management (OAM) client layer 329, and a medical information database layer 331.

The kernel/device driver layer 311 is resident in the second storage unit 230, and manages devices and memory, processes and input and output connected to the inside and outside of the integrated gateway device 200.

The system API layer 313 performs interfacing between the kernel and device driver of the kernel/device driver layer 311 and application programs.

In order to provide web-based remote monitoring and control, the graphic user interface GUI layer 317 provides a graphic user interface in the case of access of the user terminal or provides a graphic user interface in the case of direct access of a console.

Since the kernel/device driver layer 311, the system API layer 313 and the GUI layer 317 have general-purpose configurations, detailed descriptions thereof will be omitted here.

The medical information layer 316 includes a medical information integration sublayer and a medical instrument support sublayer, and manages medical instrument information, protocol information, and channel allocation information. The medical information integration sublayer collects and integrates a plurality of pieces of measured medical data created by the medical instruments 110, that is, perform data processing in compliance with protocols. The medical instrument support layer manages device information regarding the medical instruments connected to the integrated gateway device 200, channel allocation information, and profiling information.

The digital data processing layer 319 performs data exchange and processing between the integrated gateway device 200 and the medical instruments 110 and between the integrated gateway device 200 and the hospital server 140, performs schedule according to the importance of data, and distinguishes between and then processing real-time data and non-real-time data.

The QoS/logging layer 321 monitors various types of performance quality of the integrated gateway device 200 such as communication quality, quality regarding the success/failure of data exchange and CPU usage, and stores records.

The system setting layer 323 performs various types of setting and updating of the integrated gateway device 200 through the web or console.

The Expert Alg layer 325 performs the verification of the validity of measured data, automatic user recognition using measured data, the checking of a data collection pattern by the checking of a data transmission period, the correction of various types of errors and noise, and user alarm and warning regarding an excess of a threshold value.

The Operations, Administration And Maintenance (OAM) client layer 329 supports the remote management of the system. That is, when the user terminal 120 controls the medical instruments 110 from a remote location through the web, the OAM client layer 329 operates as a subject which actually commands that the medical instruments 110 be controlled.

The communication messaging layer 327 supports various types of international standards, such as HL7 and HL7 CDA, in the communication with the hospital server. That is, the communication messaging layer 327 performs message processing and manages sent and received messages between the user terminal 120 and the hospital server 150 over the wired/wireless communication network 130.

The medical information database layer 331 is an element corresponding to the medical information DB 280, and stores and manages patients' personal information, that is, patient information, and medical measurement results data measured by the medical instruments 110 in the medical information DB 280.

Figure 6:
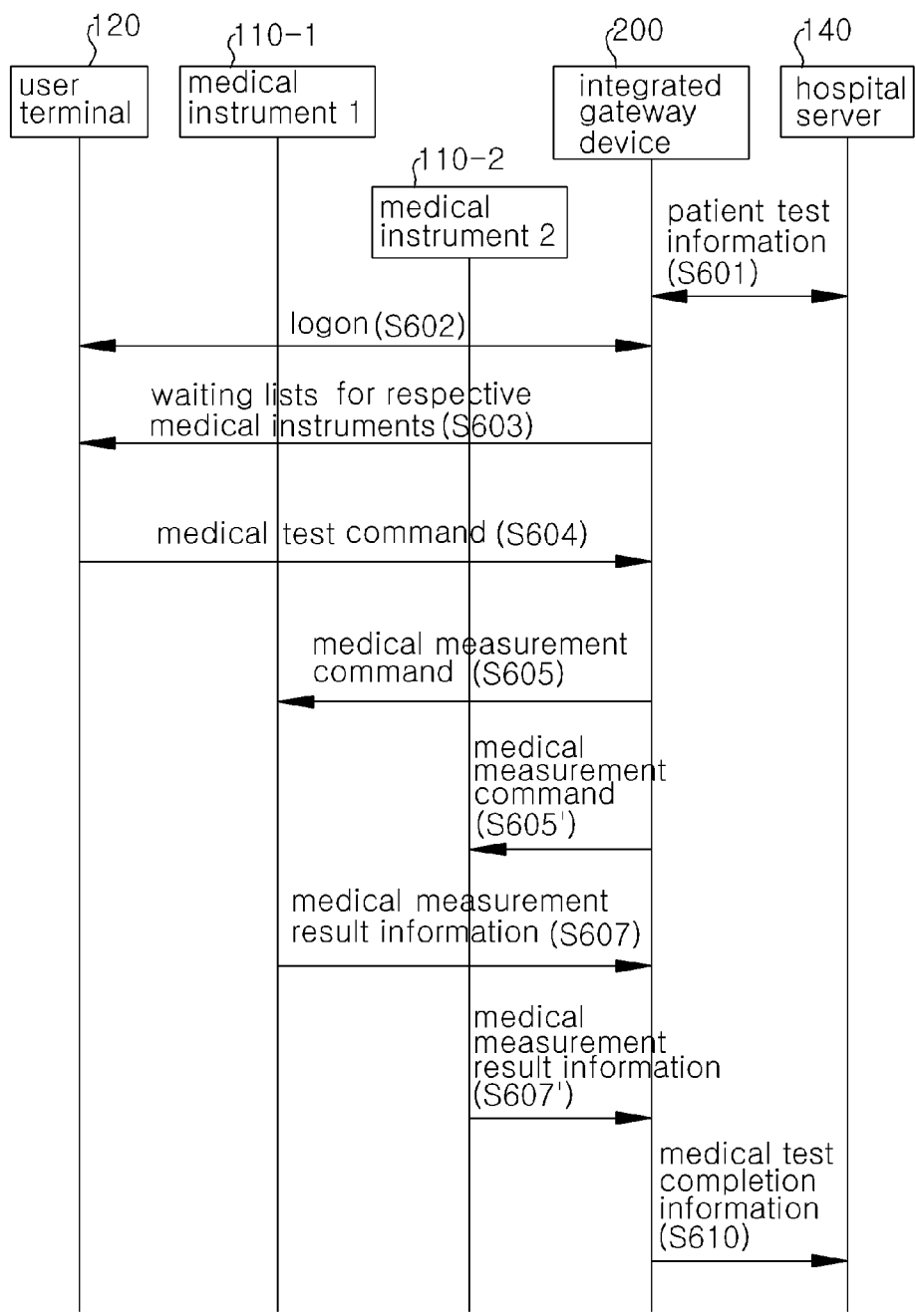
FIG. 6 is a diagram showing a procedure of a method of supporting information interoperability between medical instruments in the system for supporting information interoperability between medical instruments according to the present invention.
Figure 7:
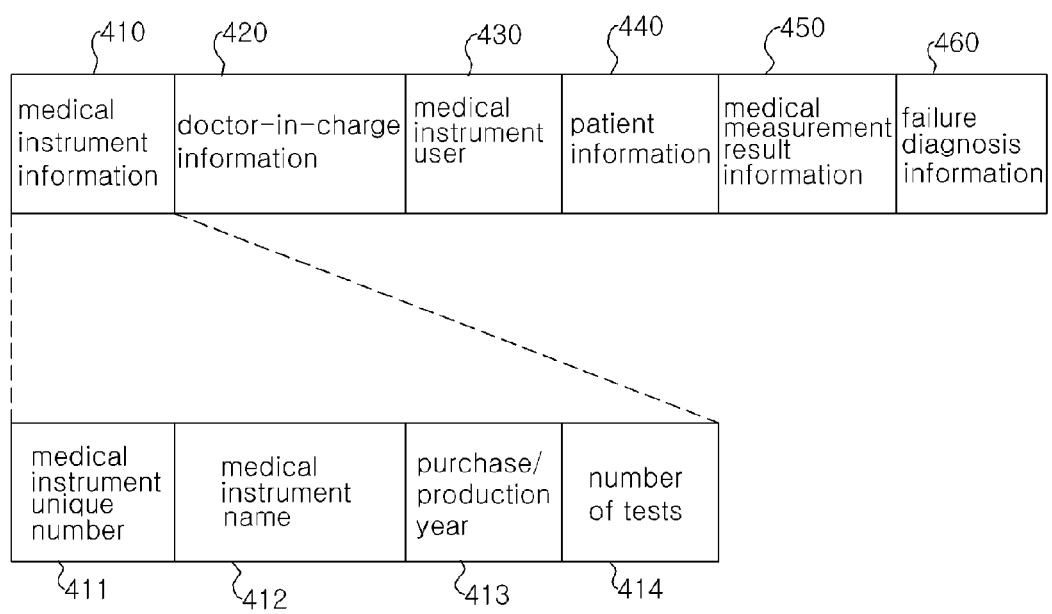
FIG. 7 is a view showing the format of a medical test completion information message sent from the integrated gateway device.

FIG. 6 is a diagram showing a procedure of a method of supporting information interoperability between medical instruments in the system for supporting information interoperability between medical instruments according to a first embodiment of the present invention, and FIG. 7 is a view showing the format of a medical test completion information message transmitted from the integrated gateway device to the user terminal and the hospital server according to the present invention. Referring to FIGS. 6 and 7, the method of supporting information interoperability between medical instruments according to the first embodiment of the present invention will be described below.

First, when a test event occurs, the hospital server 140 sends patient test information to the integrated gateway device 200 at step S601. The test event may be the reception of a scheduled patient who will be tested using a medical instrument 110 or the scheduling of the use of a medical instrument 110 after a doctor in charge has made a diagnosis. The patient test information may include information about a doctor in charge, a patient, a diagnosis or a medical instrument.

When the patient test information is received from the hospital server 140, the integrated gateway device 200 performs registration in waiting lists for respective medical instruments, and sends the waiting lists for respective medical instruments to the user terminal 120 at step S603. At this time, the user terminal 120 must have logged on to the integrated gateway device 200. If the user terminal 120 has not logged on, the waiting lists for respective medical instruments, together with web-based GUI data, are sent at step S603 at the moment the user terminal 120 logs on to and accesses the integrated gateway device 200 at step S602.

The user terminal 120 having received the waiting lists for respective medical instruments sends a medical test command to the integrated gateway device 200 according to the waiting lists for respective medical instruments at step S604.

The integrated gateway device 200 having received the medical test command sends a medical measurement command to a corresponding medical instrument 110 at step S605. The medical measurement command includes medical instrument information and a operation command.

The medical instrument 110 having received the medical measurement command performs medical measurement in conformity with the operation command included in the received medical measurement command, and sends medical measurement result information based on the performed measurement to the integrated gateway device 200 at step S607. The measurement result information may further include medical instrument information.

The integrated gateway device 200 having received the medical measurement result information sends medical test completion information to the hospital server 140 at step S610. The medical test completion information, as shown in FIG. 7, includes medical instrument information, doctor-in-charge information, medical instrument user information, patient information, and medical measurement result information. Furthermore, the medical instrument information includes information about the unique number of a medical instrument, the name of a medical instrument, a purchase/production or registration year, and the number of test.

Furthermore, when receiving the medical measurement result information, the integrated gateway device 200 further creates failure diagnosis information by analyzing whether an error has occurred in the state of communication with the corresponding medical instrument 110 and the medical measurement result data based on the medical measurement command. Thereafter, the integrated gateway device 200 includes the created failure diagnosis information in the medical test completion information, as shown in FIG. 7, and sends the resulting data to the hospital server 140.

The hospital server 140 analyzes the medical test completion information received at step S610, and stores the measured data obtained by the medical instrument 110 in association with the EMR of a corresponding patient stored in the database 150.

Figure 8:
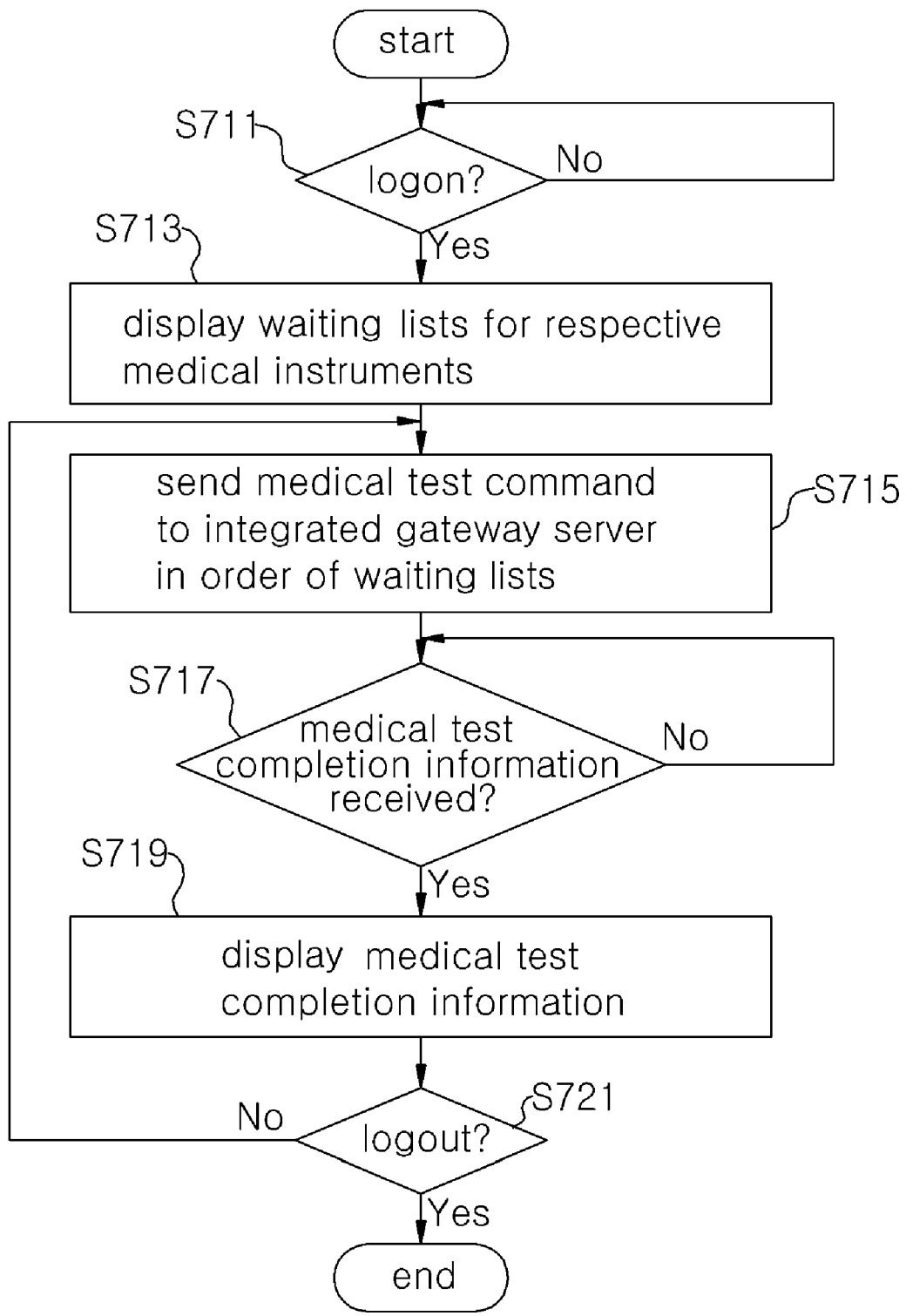
FIG. 8 is a diagram showing a method of supporting information interoperability between medical instruments in the user terminal of the system for supporting information interoperability between medical instruments according to the present invention.

FIG. 8 is a diagram showing a method of supporting information interoperability between medical instruments in the user terminal of the system for supporting information interoperability between medical instruments according to the present invention.

Referring to FIG. 8, the user terminal 120 determines whether logon information has been input, and, if logon information has been input, accesses the integrated gateway device 200 over wired/wireless network 130 at step S711.

When accessing the integrated gateway device 200, the user terminal 120 receives and displays GUI data and waiting lists for respective medical instruments at step S713.

After receiving and displaying the waiting lists for respective medical instruments, the user terminal 120 sends medical test commands to the integrated gateway device 200 in order of the waiting lists for respective medical instruments a step S715.

After sending the medical test command, the user terminal 120 checks whether medical test completion information has been received at step S717.

If the medical test completion information has been received, the user terminal 120 displays the medical test completion information at step S719, and repeats the process following step S715 until logout at step S721.

Figure 9:
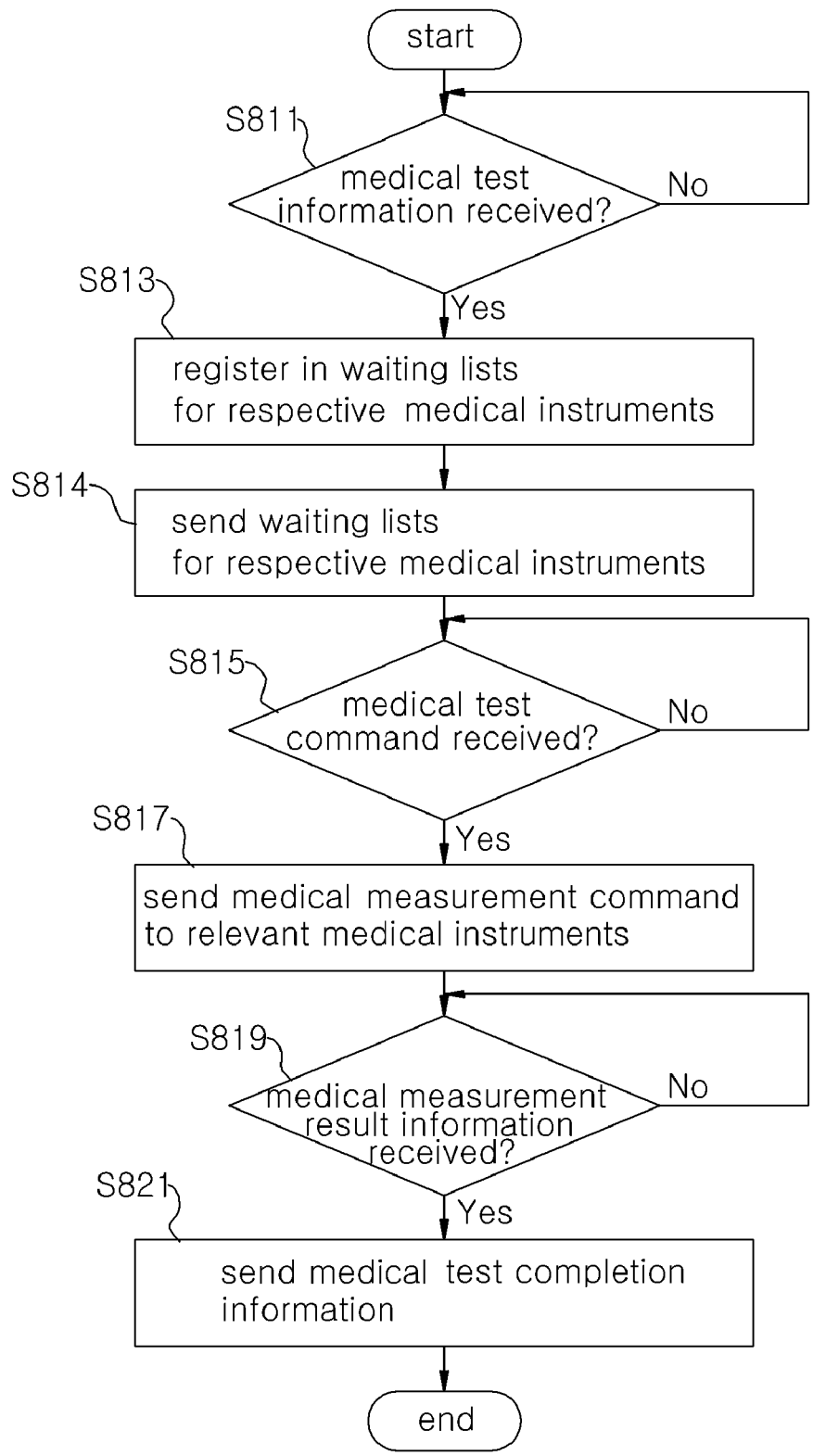
FIG. 9 is a diagram showing a method of supporting information interoperability between medical instruments in the integrated gateway device of the system for supporting information interoperability between medical instruments according to the present invention.

FIG. 9 is a diagram showing a method of supporting information interoperability between medical instruments in the integrated gateway device of the system for supporting information interoperability between medical instruments according to the present invention.

Referring to FIG. 9, the integrated gateway device 200 checks whether medical test information has been input from the hospital server 140 at step S811.

If the medical test information has been input, the integrated gateway device 200 analyzes the medical test information and registers a corresponding patient in waiting lists for respective medical instruments at step S813, and sends the waiting lists for respective medical instruments to the user terminal 120 at step S814.

After sending the waiting lists for respective medical instruments, the integrated gateway device 200 checks whether a medical test command has been received from the user terminal 120 at step S815.

If the medical test command has been received, the integrated gateway device 200 sends a medical measurement command to a corresponding medical instrument 110 at step S817, and checks whether medical measurement result information has been received in response to the medical measurement command at step S819.

If the medical measurement result information has been received, the integrated gateway device 200 creates medical test completion information and sends the information to the hospital server 140 at step S821.

Figure 10:
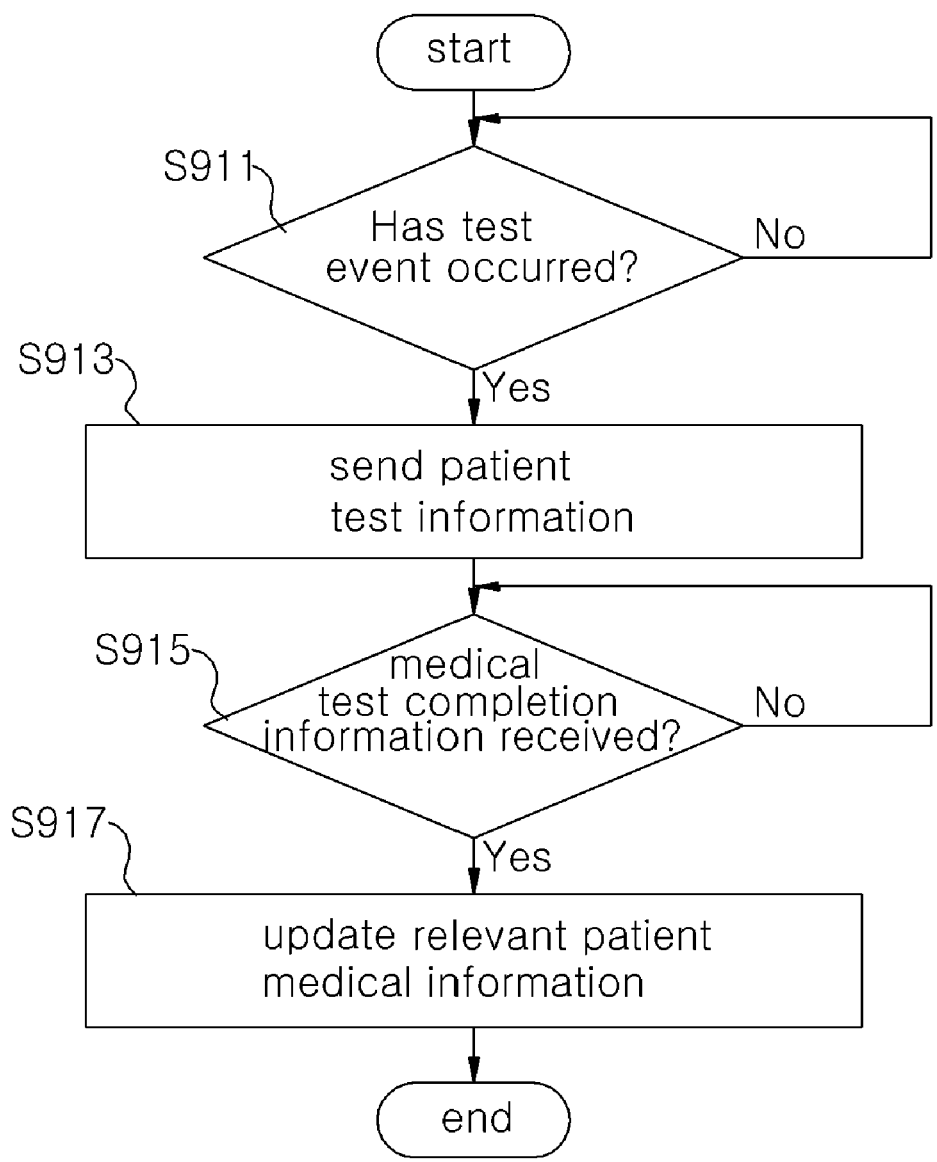
FIG. 10 is a diagram showing a method of supporting information interoperability between medical instruments in the hospital server of the system for supporting information interoperability between medical instruments according to the present invention.

FIG. 10 is a diagram showing a method of supporting information interoperability between medical instruments in the hospital server of the system for supporting information interoperability between medical instruments according to the present invention. Referring to FIG. 10, the operation of the hospital server 140 will be described below.

The hospital server 140 checks whether a test event has occurred first at step S911. A test event occurs due to the reception of the scheduling of a second test which will be performed using a medical instrument 110 or the scheduling of the use of a medical instrument 110 based on the diagnosis of a doctor in charge.

If a test event has occurred, the hospital server 140 sends patient test information to the integrated gateway device 200 at step S913.

After sending the patient test information, the hospital server 140 checks whether patient medical test completion information has been received from the integrated gateway device 200 at step S915. In this case, if the patient medical test completion information has been received, medical measurement result data is detected from the patient medical test information and is stored in association with the electronic medical information of a relevant patient at step S917.

Figure 11:
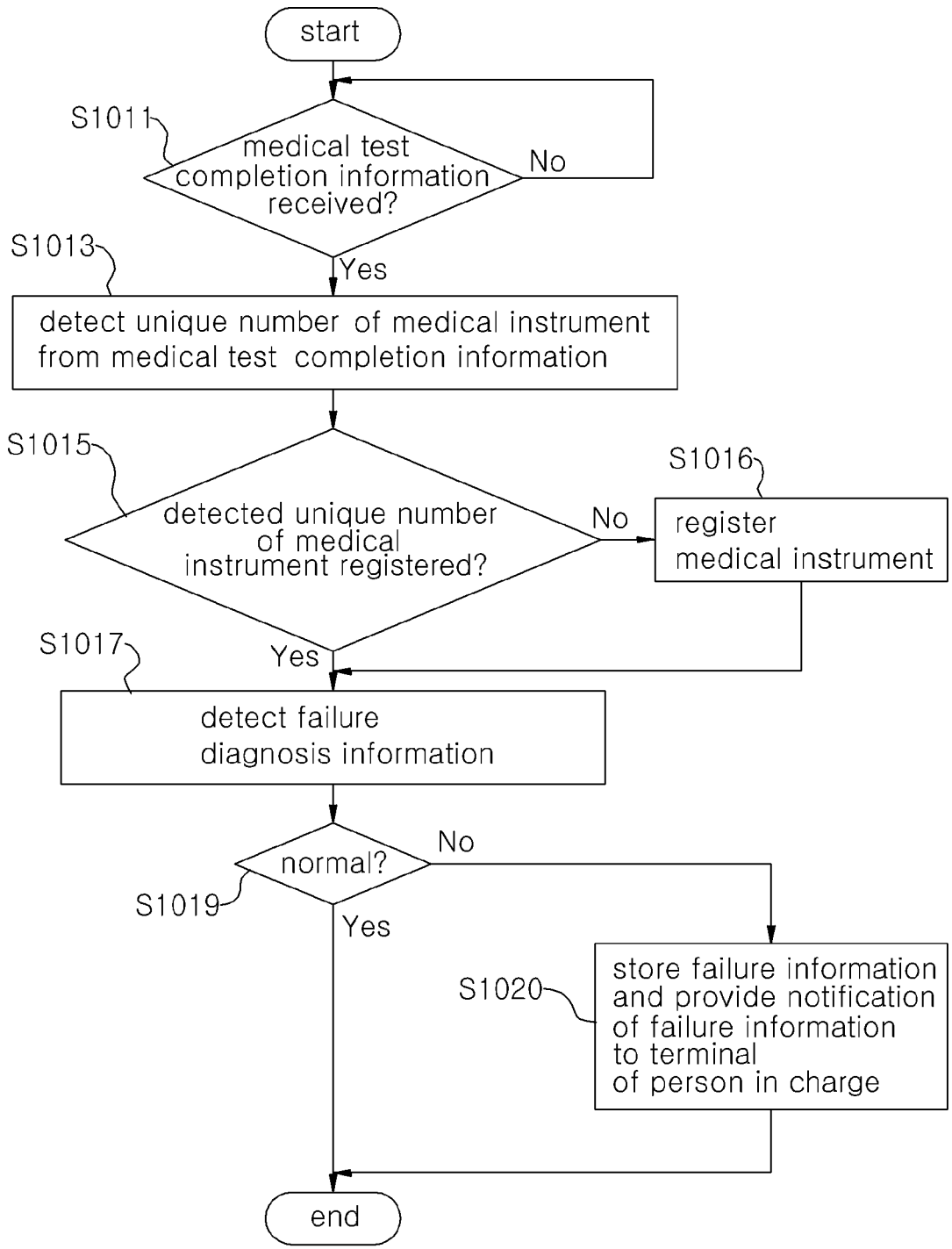
FIG. 11 is a diagram showing a method of managing medical instruments in the hospital server of the system for supporting information interoperability between medical instruments according to the present invention.

FIG. 11 is a diagram showing a method of managing medical instruments in the hospital server of the system for supporting information interoperability between medical instruments according to the present invention.

FIG. 11 shows a method of managing medical instrument assets and maintenance in the hospital server 140. For this purpose, as described above, the integrated gateway device 200 makes a failure diagnosis, includes failure diagnosis information in medical test completion information, and sends the medical test completion information.

Referring to FIG. 11, the hospital server 140 checks whether the medical test completion information has been received from the integrated gateway device 200 at step S1011.

If the medical test completion information has been received, the hospital server 140 detects the unique number of a medical instrument from the medical test completion information at step S1013.

When the unique number of the medical instrument has been detected, the hospital server 140 checks whether the measured unique number of a medical instrument has been registered at S1015. If the measured unique number has been registered, information about the unique number of the medical instrument, the name of the medical instrument, the production or registration date of the medical instrument and the number of tests included in the medical test completion information is detected and then stored and registered in the database 150 or a separate medical instruments management database (not shown) at step S1016, and then the failure diagnosis information of the medical test completion information is detected at step S1017. If the measured unique number has been registered, failure diagnosis information is immediately detected at step S1017.

The hospital server 140 detects and analyzes the failure diagnosis information and determines whether the medical instrument is normal at step S1019. If, as a result of the determination, the medical instrument is not normal, the failure information is stored and notification of the fact that the medical instrument 110 has failed is provided to the user terminal 120 of a person in charge at step S1020.

FIGS. 6 to 11 illustrate the cases where the user terminal 110 operates as a subject which issues medical test commands.

Figure 12:
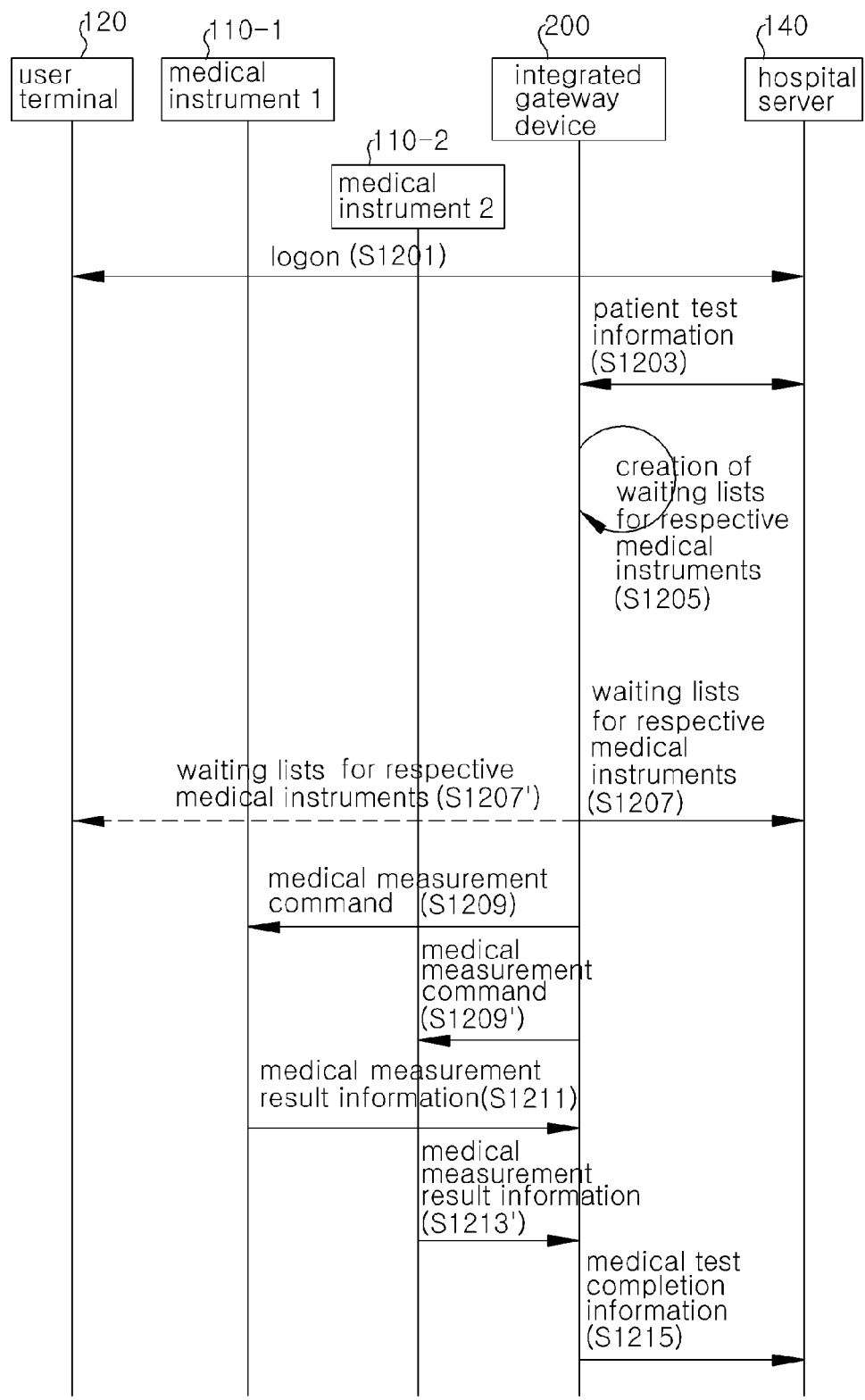
FIG. 12 is a flowchart showing a method of supporting information interoperability between medical instruments according to a second embodiment of the present invention.

FIG. 12 illustrates the case where the integrated gateway device 200 operates as a subject which issues medical test command.

FIG. 12 is a flowchart showing a method of supporting information interoperability between medical instruments according to a second embodiment of the present invention.

When a test event has occurred, the hospital server 140 sends patient test information to the integrated gateway device 200 at step S1203. The test event may be the reception of a scheduled patient who will be tested using a medical instrument 110 or the scheduling of the use of a medical instrument 110 after a doctor in charge has made a diagnosis. The patient test information may include information about a doctor in charge, a patient, a diagnosis or a medical instrument.

When the patient test information is received from the hospital server 140, the integrated gateway device 200 creates and updates waiting lists for respective medical instruments at step S1205, and sends the waiting lists for respective medical instruments to the hospital server 140 or user terminal 120 so that a doctor in charge or a person in charge of the medical instrument can check them at step S1207.

After sending the waiting lists for respective medical instruments, the integrated gateway device 200 sends a medical measurement command to a corresponding medical instrument 110 in order of the waiting lists for respective medical instruments at step S1209. In this case, the integrated gateway device 200 may simultaneously send a plurality of medical measurement commands to different medical instruments. A medical measurement command includes medical instrument information and an operation command.

The medical instrument 110 having received the medical measurement command performs medical measurement in conformity with an operation command included in the received medical measurement command, and sends medical measurement result information based on the performed measurement to the integrated gateway device 200 at step S1211. The medical measurement result information may further include medical instrument information depending on a medical instrument.

The integrated gateway device 200 having received the medical measurement result information sends received medical test completion information to the hospital server 140 at step S1213. The medical test completion information, as shown in FIG. 7, includes medical instrument information, doctor-in-charge information, medical instrument user information, patient information, and medical measurement result information. Furthermore, the medical instrument information includes information about the unique number of a medical instrument, the name of a medical instrument, a purchase/production year or registration year, and the number of tests.

Furthermore, when receiving the medical measurement result information, the integrated gateway device 200 further creates failure diagnosis information by analyzing whether an error has occurred in the state of communication with the corresponding medical instrument 110 and the medical measurement result data based on the medical measurement command. Thereafter, the integrated gateway device 200 includes the created failure diagnosis information in the medical test completion information, as shown in FIG. 7, and sends the resulting data to the hospital server 140.

The hospital server 140 analyzes the medical test completion information received at step S1213, and stores the measured data obtained by the medical instrument 110 in association with the EMR of a corresponding patient stored in the database 150.

The integrated gateway device 200 is configured to send the waiting lists for respective medical instruments only to the hospital server 140. In this case, the user terminal 120 logs in to the hospital server 140 over the wired/wireless network 130 and checks the waiting lists for respective medical instruments.

Meanwhile, it will be easily understood by those skilled in the art that the present invention is not limited only to the above-described typical preferred embodiments, but the present invention may be variously modified, varied, replaced or added within the range of the gist of the present invention. As long as the performance of the modification, variation, replacement or addition pertains to the scope of the attached claims, the technical spirit thereof must be considered to pertain to the present invention.

What is claimed is:

1. A system for supporting information interoperability between medical instruments, comprising:
    a plurality of medical instruments configured to have data interface units for sending and receiving data in compliance with preset interface protocols, and configured to, when receiving medical measurement commands via the data interface unit, perform medical measurement and then send medical measurement result information;
    an integrated gateway device configured to have a multiple interface unit comprising data interface units corresponding to the data interface units of the medical instruments, respectively, and configured to, when patient test information requesting medical measurement has been received, create and send waiting lists for respective medical instruments, send the medical measurement commands to relevant medical instruments in conformity with the received medical test command, and send medical test completion information, including the medical measurement result information received in response to the medical measurement commands, via a wired/wireless (wired, wireless or hybrid wired-wireless) communication network;
    one or more user terminals configured to, when the waiting lists for respective medical instruments have been received, send medical test commands based on the waiting lists for respective medical instruments to the integrated gateway device; and
    a hospital server configured to have a database for storing Electronic Medical Record (EMR) information including medical measurement information, and configured to, when a test event has occurred, send the patient test information to the integrated gateway device, receive medical test completion information in response to the patient test information, and store the medical test completion information in association with relevant patient information of the EMR information,
    wherein the integrated gateway device comprises:
    a multiple interface unit comprising data interface units which correspond to the data interface units of the medical instruments, respectively;
    a first storage unit storing middleware capable of performing communication with the medical instruments which may be connected to the multiple interface unit and processing data for the communication;
    a wired/wireless communication unit for, when the medical test command is received, sending the medical test completion information to the wired/wireless communication network; and
    a control unit for, when the medical test command is received via the communication unit, sending a medical measurement command via the multiple interface unit, collecting pieces of medical measurement result information received in response to the medical test command and creating the medical test completion information, and sending the medical test completion information via the wired/wireless communication unit,
    wherein the middleware comprises:
    a medical information layer for managing the medical instrument information, protocol information and channel allocation information, process data to be received and sent from and to the medical instruments in compliance with the protocols, and collecting and integrating received measured medical data;
    a digital data processing layer for processing data exchange between the integrated gateway device and the medical instruments and between the integrated gateway device and the hospital server;
    a QoS/logging layer for monitoring communication quality, and Quality regarding success/failure of the data exchange;
    an Expert Alg layer for verifying validity of the measured data received from the medical instruments, automatic user recognition, data collection pattern checking and error and noise correction based on the measured data, and handling alarm and warning regarding an excess of a threshold value;
    an Operations, Administration and Management (OAM) client layer for supporting control of the medical instruments of the user terminal; and
    a communication messaging layer for processing and managing messages with the hospital server.

2. The system according to claim 1, wherein the multiple interface unit comprises a parallel interface unit, a serial interface unit, an asynchronous serial bus interface unit and a DICOM interface unit each having at least one port.

3. The system according to claim 2, wherein:
    the multiple interface unit further comprises an analog video interface unit; and
    the integrated gateway device further comprises a digital conversion unit for converting an analog video signal, received through the analog video interface unit, into digital image data and outputting the digital image data.

4. The system according to claim 2, wherein:
    the multiple interface unit further comprises an external memory interface unit which has a plurality of external memory slots, and which reads data from external memory inserted into the slots and outputs the data to the control unit or stores data, input from the control unit, in the external memory; and
    the control unit directs the external memory interface unit to read medical measurement result information from the external memory when a read command is input from one of the user terminals, and directs the external memory interface unit to store medical test completion information in the external memory when a write command is input from the user terminal.

5. The system according to claim 1, wherein the patient test information comprises information about a patient and a doctor in charge.

6. The system according to claim 1, wherein the medical test command comprises information about a patient, a doctor in charge, a medical instrument user and one or more relevant medical instruments.

7. The system according to claim 1, wherein the medical measurement command comprises medical instrument information and an operation command.

8. The system according to claim 1, wherein the medical measurement result information comprises medical instrument information and medical measurement result data.

9. The system according to claim 1, wherein the medical test completion information comprises information about one or more relevant medical instruments, a doctor in charge, a medical instrument user, a patient, and medical measurement result data.

10. The system according to claim 1, wherein the integrated gateway device performs a failure diagnosis by checking reception results of medical measurement result information based on the medical measurement command for the failure diagnosis, and sends the medical test completion information with failure diagnosis information based on the performance of the failure diagnosis included therein.

* * * * *